(12) United States Patent
Carpentier et al.

(10) Patent No.: US 8,942,781 B2
(45) Date of Patent: Jan. 27, 2015

(54) MEDICAL SYSTEM COMPRISING A PERCUTANEOUS PROBE

(75) Inventors: Alexandre Carpentier, Paris (FR); Julian Itzcovitz, Neuilly sur Seine (FR)

(73) Assignees: Universite Pierre et Marie Curie (Paris 6), Paris (FR); Assistance Publique Hopitaux de Paris, Paris (FR)

( * ) Notice: Subject to any disclaimer, the term of this patent is extended or adjusted under 35 U.S.C. 154(b) by 324 days.

(21) Appl. No.: 12/937,166

(22) PCT Filed: Apr. 9, 2009

(86) PCT No.: PCT/EP2009/054319
§ 371 (c)(1),
(2), (4) Date: Oct. 8, 2010

(87) PCT Pub. No.: WO2009/125002
PCT Pub. Date: Oct. 15, 2009

(65) Prior Publication Data
US 2011/0040172 A1    Feb. 17, 2011

Related U.S. Application Data

(60) Provisional application No. 61/043,501, filed on Apr. 9, 2008.

(51) Int. Cl.
A61B 5/05        (2006.01)
A61B 8/08        (2006.01)
(Continued)

(52) U.S. Cl.
CPC .............. *A61B 8/0833* (2013.01); *A61B 5/0068* (2013.01); *A61B 5/0084* (2013.01);
(Continued)

(58) Field of Classification Search
USPC .......... 600/407, 437, 473, 476, 410; 601/2, 3; 604/48, 93.01, 164.01
See application file for complete search history.

(56) References Cited

U.S. PATENT DOCUMENTS 5,492,126 A    2/1996   Hennige et al. .......... 128/660.03
5,665,054 A    9/1997   Dory ................................ 601/3
(Continued)

FOREIGN PATENT DOCUMENTS

CN    2853097 Y    1/2007
CN    1966108 A    5/2007
(Continued)

OTHER PUBLICATIONS

Fennessy et al., "Magnetic Resonance Imaging-Guided Interventions in the Genitourinary Tract: An Evolving Concept", Jan. 2008, Radiol Clin North Am., pp. 1-28.*
(Continued)

*Primary Examiner* — James Kish
(74) *Attorney, Agent, or Firm* — Seed IP Law Group PLLC

(57) ABSTRACT

The percutaneous probe, made in MRI-compatible materials, comprises: a body percutaneously inserted into the tissue of a patient's body organ (8) having a region (10) to be analyzed, treated and monitored during a single medical procedure; at least one information collection sensing device (30,33,34); treatment application transducers (30) 360° disposed to emit focused or defocused therapeutic ultra-sound waves. The computerized system comprises a parametrizable command device (50) adapted to simulate then command a generation of the therapeutic ultra-sound waves, and to monitor the treatment by thermal MRI images.

29 Claims, 9 Drawing Sheets

(51) Int. Cl.

| | | |
|---|---|---|
| *A61B 5/00* | (2006.01) | |
| *A61B 8/12* | (2006.01) | |
| *A61N 7/02* | (2006.01) | |
| *A61B 5/01* | (2006.01) | |
| *A61B 5/0402* | (2006.01) | |
| *A61B 5/0476* | (2006.01) | |
| *A61B 5/055* | (2006.01) | |
| *A61B 17/00* | (2006.01) | |
| *A61B 19/00* | (2006.01) | |
| *A61N 7/00* | (2006.01) | |

(52) U.S. Cl.
CPC ............. *A61B5/6848* (2013.01); *A61B 8/12* (2013.01); *A61N 7/02* (2013.01); *A61B 5/01* (2013.01); *A61B 5/0402* (2013.01); *A61B 5/0476* (2013.01); *A61B 5/055* (2013.01); *A61B 2017/00084* (2013.01); *A61B 2017/00911* (2013.01); *A61B 2019/5236* (2013.01); *A61B 2019/528* (2013.01); *A61N 2007/0073* (2013.01); *A61N 2007/025* (2013.01)
USPC .......... 600/407; 600/410; 600/411; 600/437; 601/2; 601/3; 604/48; 604/93.01; 604/164.01

(56) References Cited

U.S. PATENT DOCUMENTS

| | | | |
|---|---|---|---|
| 5,697,897 A | 12/1997 | Buchholtz et al. ............. 604/22 |
| 5,719,700 A | 2/1998 | Corcuff et al. ............. 359/368 |
| 5,926,592 A | 7/1999 | Harris et al. ............. 385/33 |
| 6,379,320 B1 * | 4/2002 | Lafon et al. ............. 601/3 |
| 6,425,867 B1 * | 7/2002 | Vaezy et al. ............. 600/439 |
| 6,461,314 B1 | 10/2002 | Pant et al. |
| 7,338,439 B2 | 3/2008 | Kanai ............. 600/176 |
| 7,520,856 B2 * | 4/2009 | Vaezy et al. ............. 600/439 |
| 7,591,794 B2 | 9/2009 | Lacoste et al. ............. 601/2 |
| 7,769,426 B2 * | 8/2010 | Hibner et al. ............. 600/411 |
| 8,216,216 B2 | 7/2012 | Warnking et al. |
| 8,327,521 B2 | 12/2012 | Dirksen et al. |
| 2003/0004439 A1 | 1/2003 | Pant et al. ............. 601/2 |
| 2003/0018255 A1 | 1/2003 | Martin et al. ............. 600/437 |
| 2003/0099264 A1 | 5/2003 | Dantus et al. ............. 372/25 |
| 2003/0130575 A1 | 7/2003 | Desai ............. 600/417 |
| 2004/0133195 A1 | 7/2004 | Solomon ............. 606/41 |
| 2005/0085726 A1 * | 4/2005 | Lacoste et al. ............. 600/439 |
| 2005/0228229 A1 | 10/2005 | Harris ............. 600/168 |
| 2005/0240170 A1 | 10/2005 | Zhang et al. ............. 606/27 |
| 2006/0206105 A1 | 9/2006 | Chopra et al. ............. 606/27 |
| 2007/0073135 A1 | 3/2007 | Lee et al. ............. 600/407 |
| 2007/0106157 A1 | 5/2007 | Kaczkowski et al. |
| 2007/0167808 A1 | 7/2007 | Nozaki ............. 600/459 |
| 2007/0207511 A1 | 9/2007 | Lee et al. ............. 435/7.23 |
| 2007/0239011 A1 | 10/2007 | Lau et al. ............. 600/439 |
| 2007/0244046 A1 | 10/2007 | Gutova et al. ............. 514/12 |
| 2008/0004528 A1 * | 1/2008 | Fitzsimons et al. ............. 600/439 |
| 2008/0139973 A1 | 6/2008 | Wang et al. ............. 601/3 |
| 2008/0221448 A1 | 9/2008 | Khuri-Yakub et al. |
| 2008/0275342 A1 | 11/2008 | Barthe et al. ............. 600/439 |
| 2008/0287837 A1 | 11/2008 | Makin et al. ............. 601/2 |
| 2009/0036774 A1 | 2/2009 | Weng et al. ............. 600/439 |
| 2009/0318003 A1 | 12/2009 | Hossack et al. |

FOREIGN PATENT DOCUMENTS

| | | |
|---|---|---|
| DE | 199 40 421 A1 | 5/2000 |
| EP | 0 643 982 A1 | 3/1995 |
| EP | 1 090 658 A1 | 4/2001 |
| EP | 1 132 054 A1 | 9/2001 |
| EP | 1 858 591 | 9/2006 |
| EP | 1 774 989 A2 | 4/2007 |
| EP | 1 837 051 A1 | 9/2007 |
| EP | 1 847 294 A1 | 10/2007 |
| EP | 2 026 739 | 12/2007 |
| FR | 2 849 781 A1 | 7/2004 |
| JP | 6-78945 | 3/1994 |
| JP | 8-33666 | 2/1996 |
| JP | 2002-148518 | 5/2002 |
| JP | 2002-282000 | 10/2002 |
| JP | 2005-080769 | 3/2005 |
| JP | 2005-121967 | 5/2005 |
| JP | 2006-068204 | 3/2006 |
| JP | 2007-000262 | 1/2007 |
| JP | 2007-000263 | 1/2007 |
| JP | 2007-128095 | 5/2007 |
| KR | 10-2007-0094620 | 9/2007 |
| WO | WO 94/09363 | 4/1994 |
| WO | WO 96/39079 | 12/1996 |
| WO | WO 99/37364 | 7/1999 |
| WO | WO 00/45706 | 8/2000 |
| WO | WO 03/005894 A1 | 1/2003 |
| WO | WO 03/090613 A1 | 11/2003 |
| WO | WO 03/096900 A2 | 11/2003 |
| WO | WO 2004/008952 A1 | 1/2004 |
| WO | WO 2004/034524 A2 | 4/2004 |
| WO | WO 2004/069072 A2 | 8/2004 |
| WO | WO 2006/097661 A1 | 9/2006 |
| WO | WO 2007/082495 A1 | 7/2007 |
| WO | WO 2007/124458 A2 | 11/2007 |
| WO | WO 2007/129166 A2 | 11/2007 |
| WO | WO 2007/143686 A2 | 12/2007 |
| WO | WO 2008/022172 A2 | 2/2008 |
| WO | WO 2008/046031 A2 | 4/2008 |

OTHER PUBLICATIONS

Meyer, Paul; Anderson, J.W.; Branson, Krautkramer. Screenshot of http://www.ndt.net/article/wcndt00/papers/idn151/idn151.htm Priority Dates back to Apr. 19, 2001, as show in screenshot by WayBack Machine's Internet Archive. Lewistown, PA.*

Carpentier et al., "Real-Time Magnetic Resonance-Guided Laser Thermal Therapy for Focal Metastatic Brain Tumors," *Neurosurgery* 63(ONS Suppl. 1):ONS21-ONS29, 2008.

International Search Report for International Application No. PCT/EP2009/054319, mailed Jul. 15, 2009, 3 pages.

Written Opinion for International Application No. PCT/EP2009/054319, mailed Oct. 9, 2010, 10 pages.

* cited by examiner

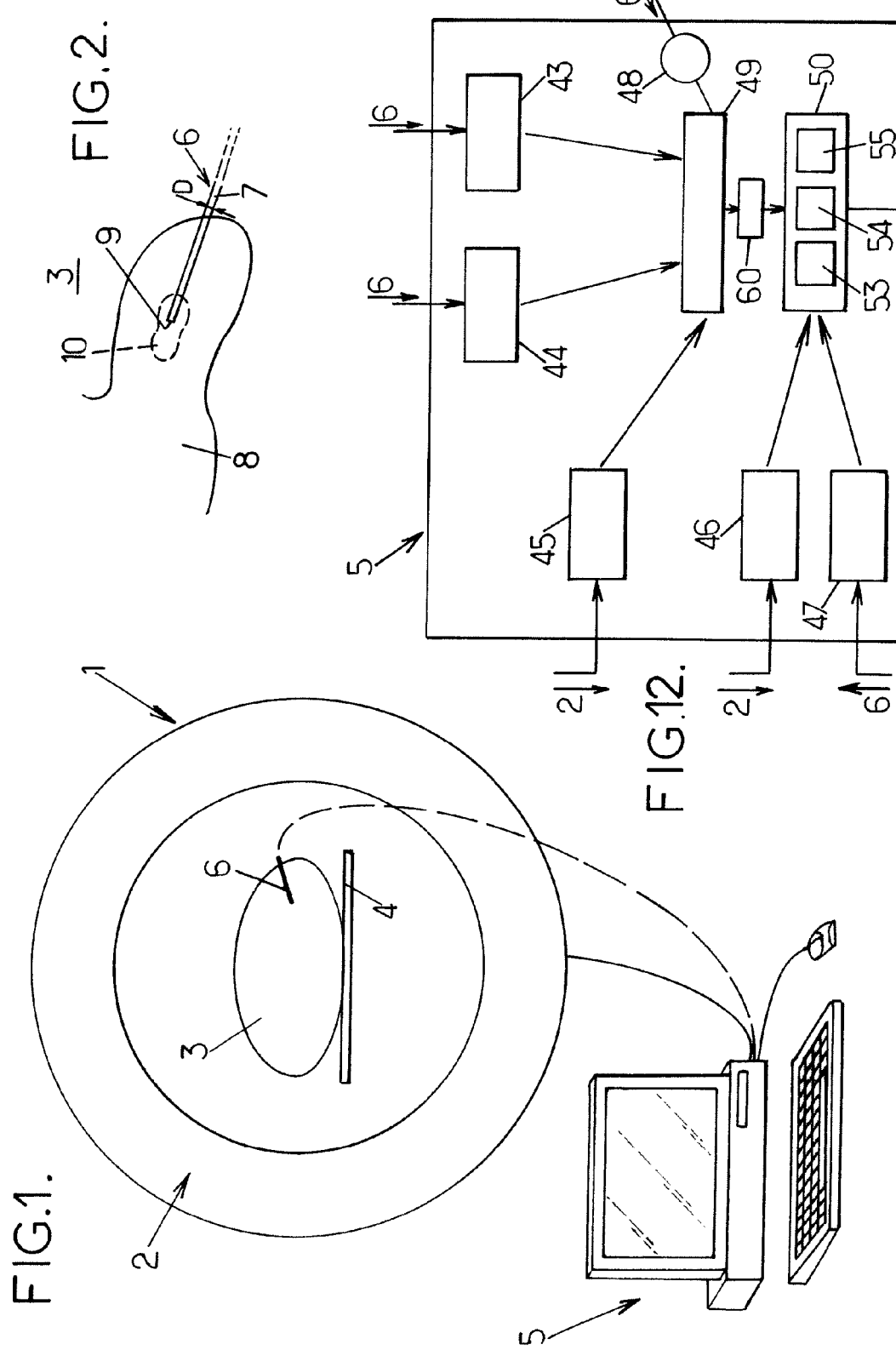

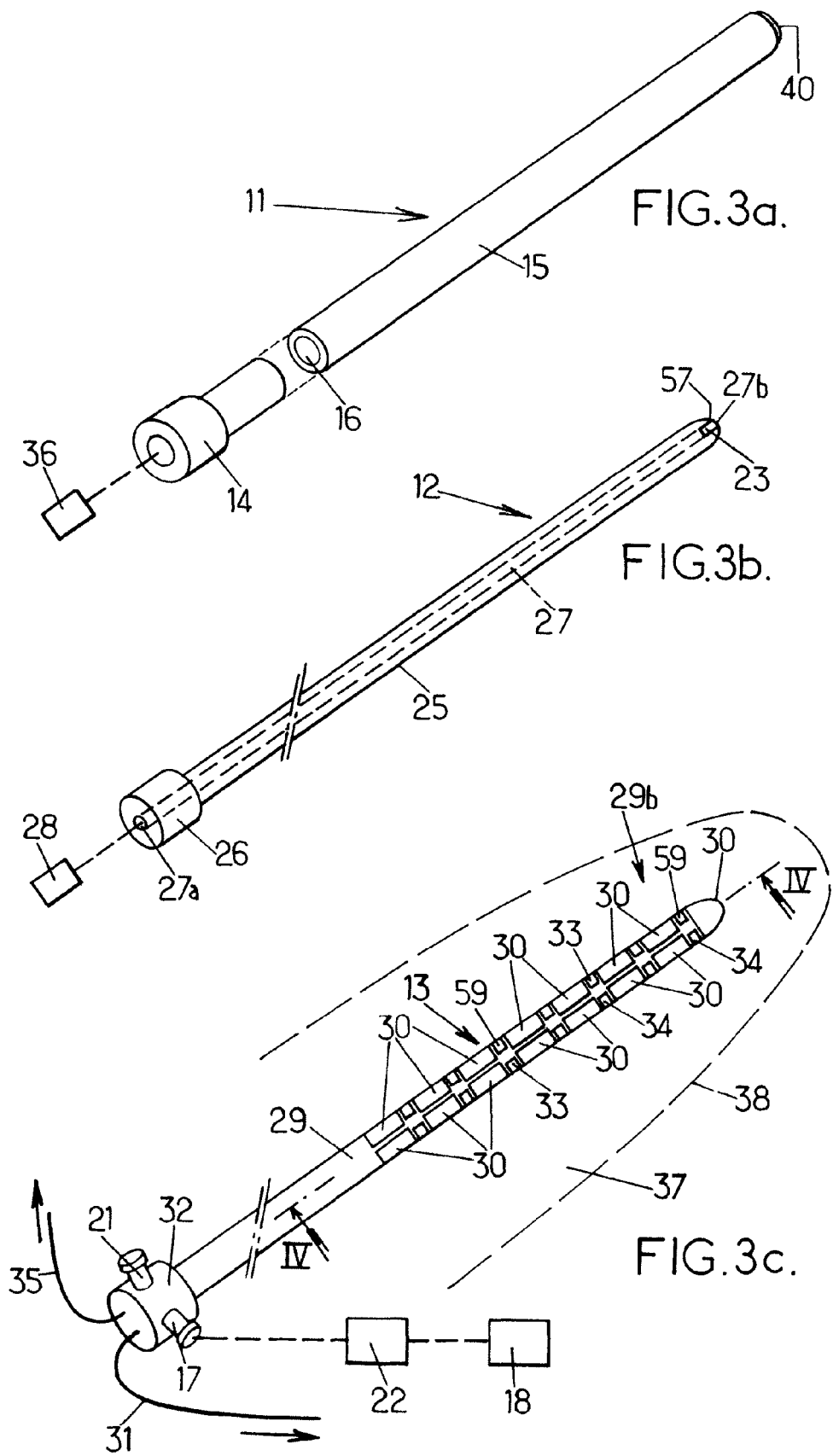

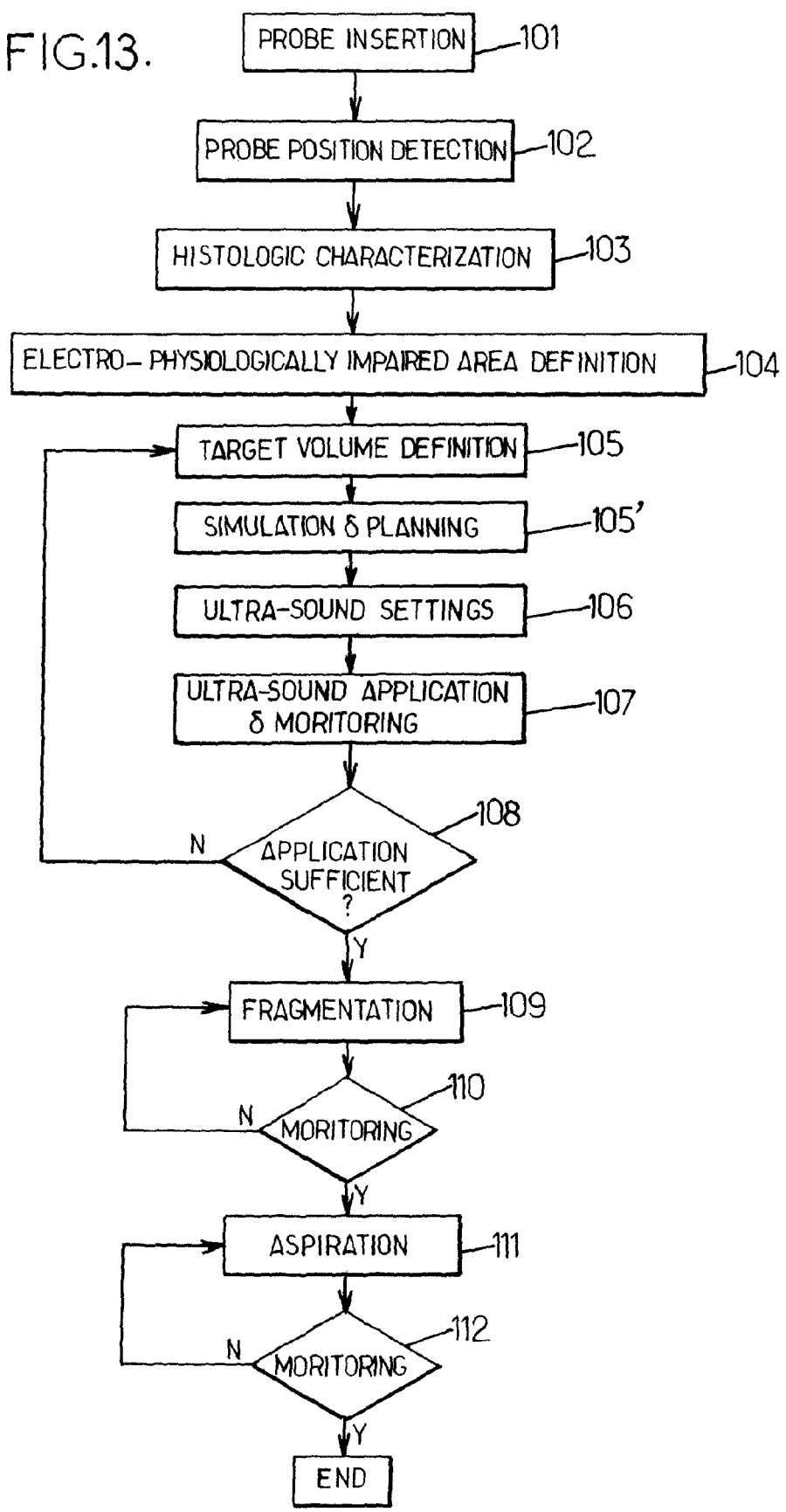

US 8,942,781 B2

MEDICAL SYSTEM COMPRISING A PERCUTANEOUS PROBE

FIELD OF THE INVENTION

The instant invention relates to medical systems comprising percutaneous probes, and to uses of such medical systems.

BACKGROUND OF THE INVENTION

Low intensity ultrasounds are widely used in medicine for diagnostic procedures, i.e. echography. For 10 years, high intensity ultra-sounds have shown to be an efficient means to induce tissue necrosis by hyperthermia for treatment procedures. Various therapeutic probes have been designed for minimally invasive therapeutic procedures and can be classified in two groups: external probes and internal probes.

External probes are designed to mimic the shape of the surface of the patient's body. Ultrasound transmitters are displayed in a concentric fashion to optimise the ultrasound waves focalization.

Internal/interstitial probes are inserted inside the body of the patient. There are three main categories: endo-cavity, endovascular or percutaneous probes.

A. Endocavity Probes

Endocavity probes are designed to be introduced in natural body holes such as the rectum, the vagina or the oesophagus. For example, US 2007/239,011 describes a medical probe for the delivery of high intensity focused ultra-sound (HIFU) energy to a patient's organ. Such a probe comprises a plane-shaped probe body inserted through a natural cavity of a patient, and a plurality of leaves to be applied to the surface of the organ, to deliver ultra-sound energy to the inside of the organ.

B. Endovascular Probes

Endovascular flexible probes are in development to treat cardiac atrial fibrillation or venous insufficiency.

C. Percutaneous Interstitial Probes

Percutaneous interstitial probes have initially received poor interest since they require a tissue penetration whereas previous probes don't penetrate the tissue. Nevertheless such percutaneous interstitial probes have been proposed for treating deep-seated tumours that cannot be reached with extra-corporeal, endocavity or endovascular high-intensity focused ultrasound probe. The ultrasound source is brought as close as possible to the target in order to minimize the effects of attenuation and phase aberration along the ultrasound pathway. Most-described ultrasound percutaneous probes are sideview emission probes whose active element is water-cooled and operates at a rather high frequency (above 3 MHz) in order to promote heating. Most described ultrasound percutaneous probes are not MRI compatible so that treatment monitoring is somewhat hazardous.

For clinicians, ultrasounds are a promising technology. To extend the applicability of ultra-sound therapy to a broad variety of medical treatments, there is a need to solve the following inconveniences:

In particular, external probes, although non intrusive, have shown consistent inconvenient: ultrasound attenuation, phase aberration and ultrasound defocalization by tissue structure (bone, tissue interfaces . . . ), targeting limits do to the constant body movement (respiratory, diaphragm . . . ), long treatment duration, unknown consequences on crossed normal tissue by the ultrasounds pathway, complexity of the probes with nowadays hundreds of ultrasound transducers, complexity to make the system MRI compatible and MRI adaptable.

In particular, sideview interstitial/internal probes require clinician manipulation of the probe during treatment such as a 360° rotation or a longitudinal translation to treat the whole lesion leading to a lack of precision and reproducibility.

In particular for all existing probes, none can perform histological characterisation or tissue biopsy, meaning that a biopsy procedure is necessary days before treatment. For all existing probes, none can perform a tissue resection after the thermal treatment. Indeed, hyperthermia treatment of a tumour will gender a serious tumour volume increase (mass effect) as shown in a previous clinical trial (Carpentier & al., "Real-time Magnetic Resonance-Guided Laser Thermal Therapy of Metastatic Brain Tumors", Neurosurgery, 63 ONS Suppl 1:21-29, 2008). Such volume increase is most of the time incompatible with preservation of the normal surrounding tissue and can limit the development of such minimally invasive ultrasound therapy systems.

SUMMARY OF THE INVENTION

The instant invention aims to solve at least some of those cited inconvenients.

To this aim, it is provided a medical system comprising a percutaneous probe and a computerized system, the percutaneous probe, made in MRI-compatible materials, comprising:
  a body having an insertion end, shaped to be percutaneously inserted into tissue of a patient's body organ having a region to be analyzed, treated and monitored during a single medical procedure,
  an optical head of an endo-confocal digital microscope,
  at least one information collection sensing device, adapted to collect information about the region of the organ,
  a plurality of treatment application transducers, operable as a phased-array, adapted to emit both focused and not-focused therapeutic ultra-sound waves to the region of the organ,
  the computerized system comprising a parametrizable command device and associated equipment adapted to command a generation of the therapeutic ultra-sound wave.

With these features, the probe can be percutaneously inserted at a suitable location in any organ. Further, the probe can be used, during a single medical procedure, to sense organ information usable for establishing a diagnostic and characterization, and for implementing the appropriate therapy.

In some embodiments, one might also use one or more of the features defined in the dependant claims.

Further, it is provided a method comprising:
  providing a body organ having a region to be analyzed, treated and monitored during a single medical procedure, said organ being provided with a percutaneous probe made in MRI compliant materials, and having a body having an insertion end inserted into tissue of the body organ,
  collecting information about the region of the organ with an information collection sensing device of the probe, and with an optical head of an endo confocal microscope
  setting parameters of at least one of a focused and not-focused therapeutic ultra-sound wave to be emitted to the region of the organ with a plurality of treatment application transducers (30) of the probe, configured as a phase-array through a parametrizable command device (50) and associated equipment (56) of a computerized system.

In some embodiments, one might also use one or more of the features defined in the method dependant claims.

Advantages of one or more of these embodiments might include:
- real time monitoring of the therapy,
- tissue histologic characterization and tissue therapeutic treatment during a single procedure,
- ability to extract air bubbles from the tissue and replace them by liquid to avoid imaging artifacts,
- ability to "real-time" monitor the therapeutic process and monitor security points for the treatment,
- ability to perform continuous MRI and MR thermometry monitoring,
- ability to perform immediate post-treatment MRI imaging sequences for monitoring the therapeutic process efficiency,
- ability to treat regions either immediately around the probe and/or delocated areas,
- improved focalization/defocalization of the therapeutic ultra-sound energy, by several techniques in order to best fit the lesion geometry,
- ability to perform the therapeutic treatment even for a moving patient and/or organ,
- ultrasounds emitters organized in a 360° fashion, thereby removing the need to rotate the probe inside the organ,
- ability to treat tumors of various and complex shapes,
- diminution of the post-treatment tumoral volume,
- ability to acquire electro-encephalogram signals during the treatment.
- ability to erase movement artefacts, ultrasound attenuations, phase aberrations and/or ultrasound defocalizations,
- no requirement of a clinician manipulation during treatment, so that MRI safety and efficacy monitoring during the treatment becomes reliable,
- ability to allow real time and in vivo tissue characterisation, biopsy, post thermal tissue resection preventing post-treatment mass effect,
- disposable technology prevents inter patient contamination.

BRIEF DESCRIPTION OF THE DRAWINGS

Other characteristics and advantages of the invention will readily appear from the following description of three of its embodiments, provided as a non-limitative examples, and of the accompanying drawings.

On the drawings:

FIG. 1 is a schematic view of a medical apparatus,

FIG. 2 is a partial sectional view of a probe inserted into a body organ,

FIGS. 3a, 3b and 3c are perspective views illustrative of various components of a probe according to a first embodiment, FIG. 12 is a schematic view of a computerized system operatively associated with the probe, FIG. 13 is a diagram showing an example of use of the medical apparatus.

On the different figures, the same reference signs designate like or similar elements.

DETAILED DESCRIPTION

Figure 4:
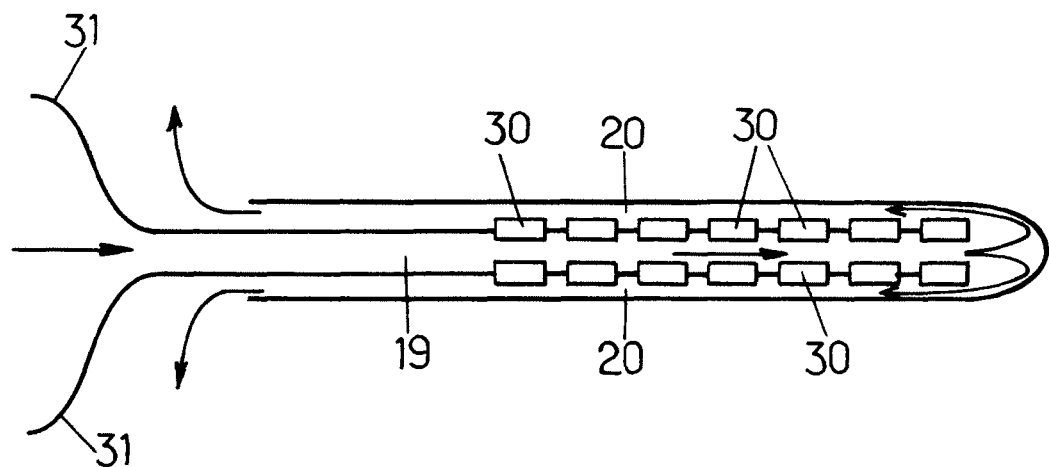
FIG. 4 is a partial sectional view along line IV-IV On FIG. 3c.

FIG. 1 is a schematic view of a medical apparatus 1 comprising a magnetic resonance imaging (MRI) system 2 of conventional type, suitable to be operated, in particular, in a thermal imaging mode, in which a patient 3 is introduced, for example lying on a suitable bed 4.

The medical apparatus 1 further comprises a computerized system 5 connected to the magnetic resonance imager so as to receive from the magnetic resonance imager data enabling the construction of anatomy and/or thermal magnetic resonance images of the patient 3.

The medical apparatus further comprises a MRI compatible probe 6 percutaneously inserted into the patient's body, and operatively associated to the computerized system 5. The probe 6 is for example electrically connected to the computerized system 5 through MRI-compatible wires, for example coaxial wires, which are known per se and will therefore not be described in more details here.

As schematically shown on FIG. 2, the probe 6 comprises a somehow cylindrical body 7 of external diameter D of 4 mm, or less, and preferably of 3 mm or less, and even more preferably of 2 mm or less, and is shaped to be introduced into the tissue of an organ 8 of the patient's body 3. The probe body 7 is interstitial, since it can be introduced directly into the tissue of the organ 8 without the necessity to go through the cavity of the organ. The insertion tip 9 of the probe body 7 is located within, or close to a region 10 of the tissue of the organ, which is to be analyzed and/or treated. The probe 6 could be applied, for example, to malignant or benign cancers, or neuro-cognitive brain impairments, as well as for other tissular pathologies of all other organs that could be treated by monitored ultrasonic treatment, such as thermal ablation.

According to a first embodiment, as shown on FIGS. 3a, 3b and 3c, the probe 6 comprises a plurality of components: an applicator 11 (FIG. 3a), a mandrel 12 (FIG. 3b), and an ultra-sound device 13 (FIG. 3c).

The applicator 11 comprises a proximally-located back portion 14 and a somehow cylindrical body 15 defining an internal cylindrical cavity 16 which extends throughout the body 15 to a tip in which an end opening 40 is formed.

The medical system can further comprise a continuous pump 36 to be placed in fluid communication with the cavity 16 of the applicator 11, or removed therefrom. The pump can thus be operated to collect tissue fragments which can later be analyzed, for example by the clinician, to provide tissue information.

The pump 36 can be operated to extract any material to be extracted from the patient, such as, for example, air bubbles that artifact images, and/or inject into the patient suitable liquids.

The inner mandrel 12 is made of a rigid material and is shaped so as to be inserted into the cavity 16 so as to totally obstruct this cavity. The mandrel 12 can for example have a body 25 of cylindrical shape, of external diameter equal to the internal diameter of the body 15 of the applicator 11. Furthermore, the mandrel 12 can have a back portion 26 of cylindrical shape of outer diameter equal to the inner diameter of the back portion 14 of the applicator 11. The mandrel 12 can further comprise a pointy tip 57. The mandrel can comprise an internal channel 27 extending from a proximal end 27a in the back portion 26, to a distal end 27b at the insertion end 9 of the probe and adapted to be placed in fluid communication with a fluid tank 28, for example through the pump 36. The pump 36 can thus be operated in connection with the mandrel 12 to insert liquid into the patient through the cavity 27 and extract air bubbles which may form artifacts on the images therefrom.

In this embodiment, the body 25 comprises, at its insertion end 9, a confocal endo-microscope head 23 which is connected through a suitable fiber extending in the cavity 27 from the confocal microscope head 23 to the back portion 14, so as to connect the confocal microscope head 23 to the computerized system 5, for example with a not-shown MRI-compatible wire. The confocal endo-microscope head can thus be used to collect in vivo and real-time cellular and tissular information of the organ.

Such miniaturized endo-confocal microscope heads are known per se and will not be described in more detail here. Alternatively, two separate channels are provided in the mandrel 25, one for fluid insertion, and one for the endoconfocal microscope fiber.

In an alternative embodiment (not shown), the mandrel back portion 26 will contain an electro mechanical component able to generate low frequency vibrations (around 10 kHz) within the mandrel body, in order to transmit low frequency vibrations to the tissue for fragmentation. In such embodiment, the mandrel might not be MRI compatible.

When the mandrel 12 is inserted through the cavity of the applicator 11, its distal portion will extend beyond the distal end of the applicator 11, so that the endo confocal microscope head will be brought in close proximity to the region to be treated.

The MRI-compatible ultra-sound device 13 has an external shape which is globally identical to the one of the mandrel 12, so as to be inserted into the cavity 16 of the applicator 11. The distal portion 29b of the body 29 of the ultra-sound device comprises a plurality of ultra-sound transducers 30 which are, for example, spaced from each other both longitudinally and circumferentially, disposed all around the circumference and the length of the part of the ultra-sound device which is to be inserted in the region to be treated. All the transducers 30 are connected as a phased-array device to the computerized control system 5 through MRI compatible wires 31, which extend from the back portion 32 of the ultra-sound device to the computerized control system 5. The transducers 30 can operate as ultra-sound emitters and/or as ultra-sound receivers. Such micro ultra-sound transducers are known per se, and will not be described in more details here (piezoelectric composite technology, capacitive micromachined ultrasonic transducers technology, etc. . . . ). When they are operated to detect ultra-sounds, the transducers thus can collect information about the organ.

The back portion 32 comprises an in-flow aperture 17 in fluid communication with a fluid tank 18 preferably provided outside the patient's body. As shown on FIGS. 4 and 5, the in-flow aperture 17 is in fluid communication with a micro circuitry of the body 29 comprising at least one in-flow channel 19 extending in the thickness of the body 29, from the back portion 32 to the tip 9 where it is in fluid communication with at least one out-flow channel 20 which extends from the tip 9 to an out-flow aperture 21 of the back portion 32.

A suitable micro pump such as a pulsed micro-pump 22 is located in the fluid line, so as to generate a flow of fluid from the fluid tank 18 to the out-flow aperture 21. Such pulsed micro-pumps are known per se and will not be described in more details here.

The outer surface of the ultra-sound device 13 can further comprise other MRI compatible sensors, such as, for example, electro-physiological signal sensors 33 such as carbon contact electrodes for detecting electro-encephalograms, electro-metabolic bio sensors 59, . . . .

Other MRI compatible sensors can be provided at the outer surface of the body 15, such as temperature sensors 34 adapted to locally detect the temperature. The sensors 33, 34 are connected to the computerized system 5 through suitable MRI compatible wires 35 extending from the back portion 32 of the ultra-sound device 13, and are thus operable to collect information about the organ.

Such micro sensors are known per se and will not be described in more details here.

When the ultra-sound device 13 is inserted through the cavity 16 of the applicator 11, its distal portion 29b will extend beyond the distal end of the applicator such that the ultra-sound transducers 30 are directly coupled to the tissue of the organ so as to emit and/or receive ultra-sounds to/from the tissue.

Figure 5:
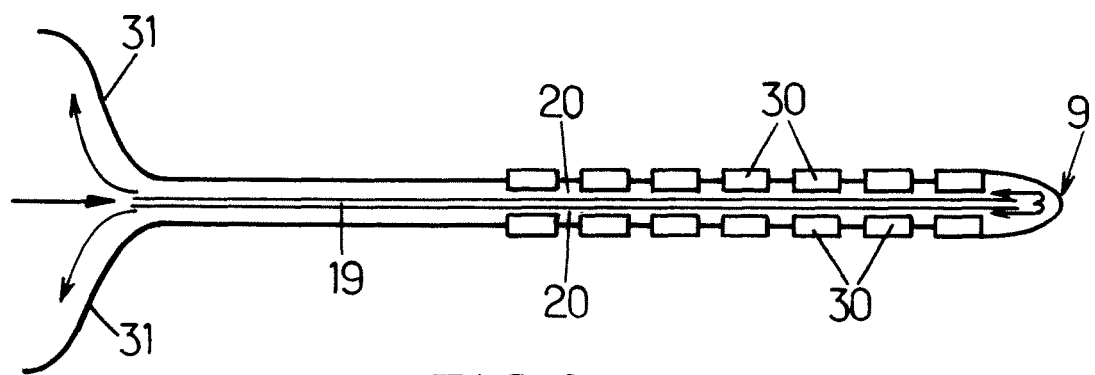
FIG. 5 is a view similar to FIG. 4 for a variant embodiment.

In the embodiment of FIG. 4, the coupling is performed by way of circulating the cooling fluid in the micro-circuitry 19, 20. As shown by FIG. 5, other configurations are possible for the flow of the cooling fluid such as having the in-flow channel 19 and the out-flow channel 20 in the centre of the probe.

The transducers 30 can be configured to be operable in an operating volume 37 around the probe having an external envelope 38 located at least 20 mm from the probe (not to scale on FIG. 3c) and preferably at least 30 mm from the probe. The transducers 30 can be further configurable to focus ultra-sounds to a focal area in the operation volume. For example, the transducers 30 are configurable to focus the ultra-sounds to a focal area having between 2 (or 3) and 10 mm of diameter. In another operative mode, the ultra-sounds are not focused.

The transducers 30 are configurable to operate in one or a plurality of frequencies, for example chosen in the range extending from 500 kHz to 10 MHz. Indeed by modulating the ultrasound emission frequencies, different physical effects, biological effects and tissue treatment effects can be produced such as cavitation phenomenons, tissue fragmentation, sonoporation of the cell membranes and thermal tissue necrosis. For thermal tissue necrosis, an embodiment is optimal between 3 MHz to 10 Mhz frequencies. The transducers 30 are configurable to operate in a plurality of emission intensities, time durations, and pulsed or continuous modes. Additionally, they can operate in phase or out of phase, in a specific setup of synchronizations.

The transducers 30 are configurable to emit sufficient energy to raise the temperature by 30 degrees Celsius, preferably by 60 degrees Celsius, within less than 2 minutes, preferably less than 20 seconds, in the whole envelope 38 (cylinder of 30 mm around the probe). Possibly, they can perform this temperature rise within less than 1 second, preferably within less than 100 milliseconds, at a focal spot of 2 mm of diameter.

Thus, the probe can be set to operate in ultrasound imaging and/or elastography modes, in an ultrasound therapeutic mode or a fragmentation mode.

Figures 6A, 6B, 6C:
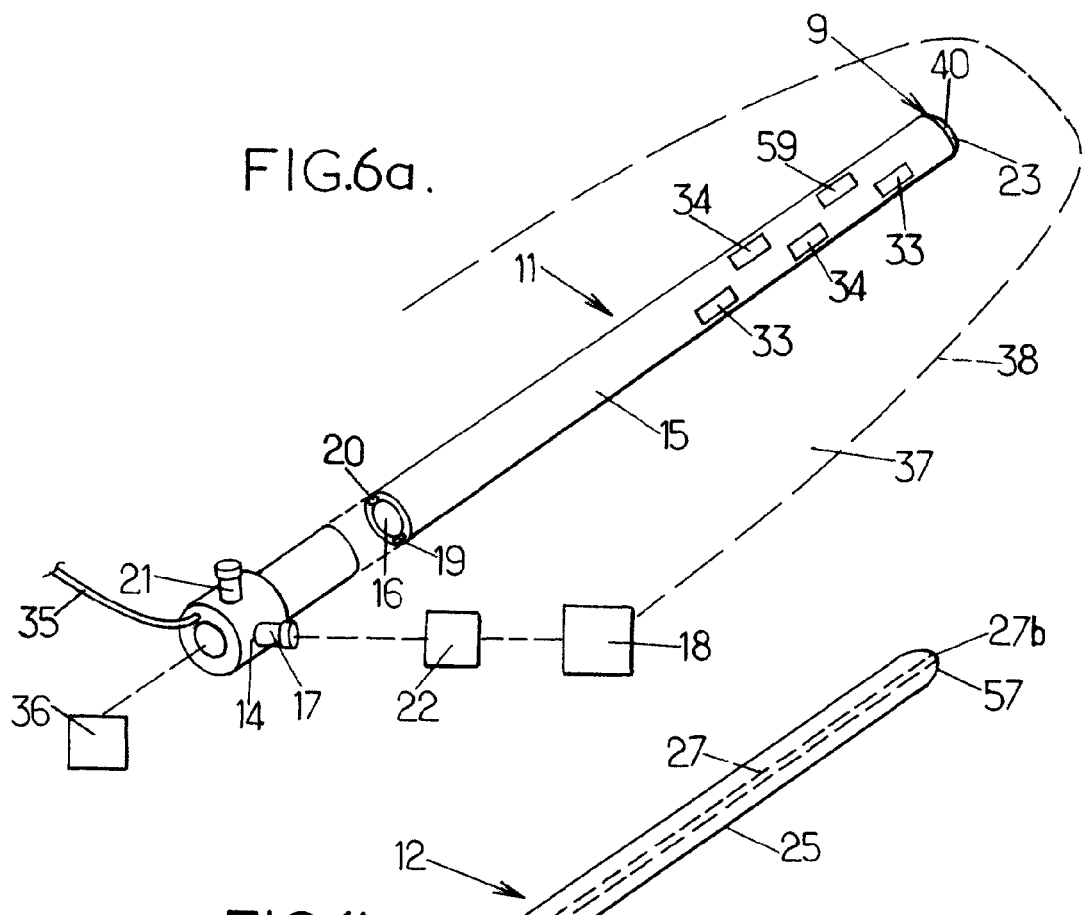
FIGS. 6a, 6b and 6c are perspective views illustrative of various components of a probe according to a second embodiment.

As can be visible from the various embodiments described in the application, other arrangements and configurations are possible within the scope of the invention. For example, a second embodiment is shown on FIGS. 6a to 6c. This second embodiment differs from the first embodiment described above in relation to FIGS. 3a to 5 mainly by the fact that the cooling fluid circuits are provided within the shell of the applicator 11, as well as the sensors 33, 34 and 59 and the head 40 of the endo confocal microscope. Thus, in this embodiment, the ultra-sound transducer 30 are coupled to the tissue of the organ through the body 15 of the applicator 11.

Figure 7A:
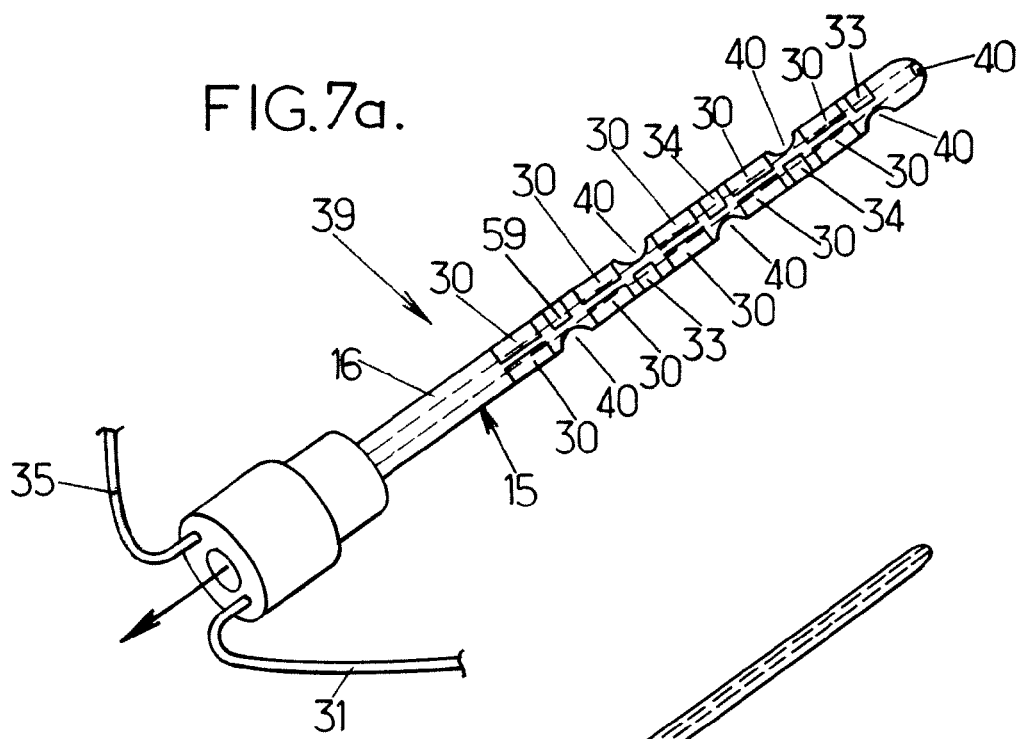
FIGS. 7a, 7b, and 7c are views similar to FIGS. 6a, 6b and 6c, respectively, for a probe according to a third embodiment.
Figure 7B:
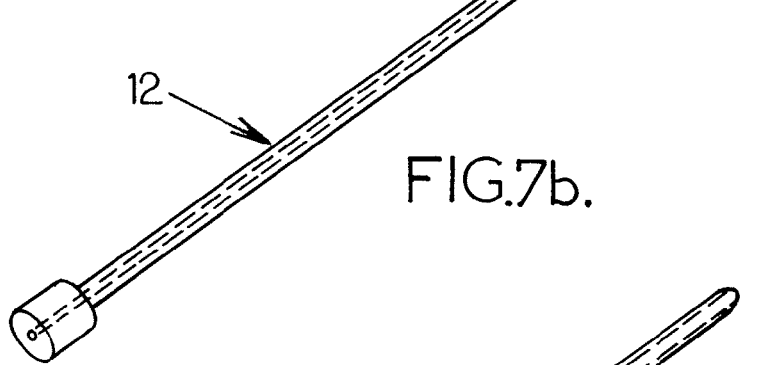
Figure 7C:
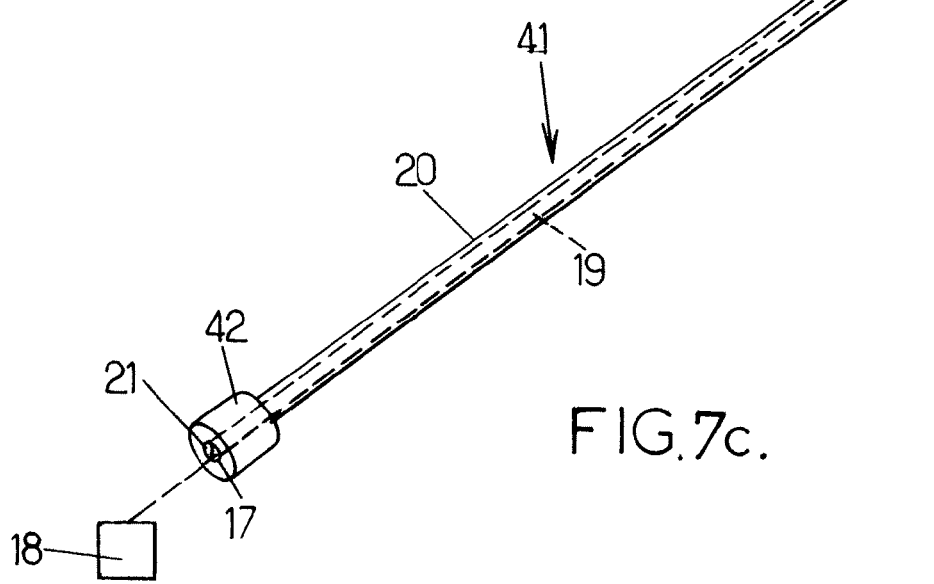

According to a third embodiment, as shown on FIGS. 7a to 7c, the applicator 11 of the second embodiment is modified to incorporate the ultra-sound transducers 30 to form a combined applicator and ultra-sound device 39. The combined device 39 further comprises a plurality of openings 40 formed on the lateral face of the body 15 and in a fluid communication with the internal cavity 16.

In this third embodiment, the probe can comprise a rigid mandrel 12 identical to the one of the second embodiment.

The probe can further comprise a cooling mandrel 41 shaped to be introduced into the internal cavity 16 of the combined device 39, and comprising a micro circuitry comprising an in-flow channel 19 in fluid communication with a fluid tank 18 through an in-flow aperture 17 of the back portion 42 of the cooling mandrel, and an out-flow channel 20 in fluid communication with the in-flow channel and exiting from the back portion 42 at an out-flow aperture 21.

Figure 8A:
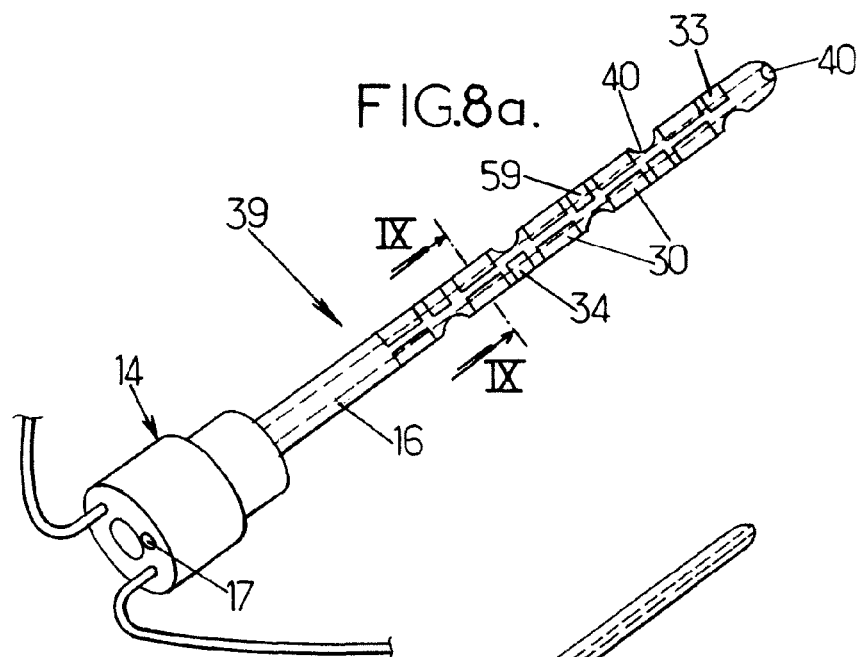
FIGS. 8a and 8b are perspective views of components of a probe according to a fourth embodiment.
Figure 8B:
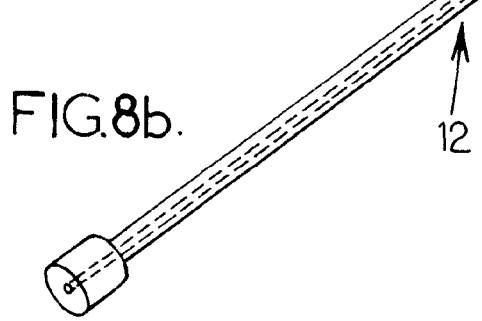
Figure 9:
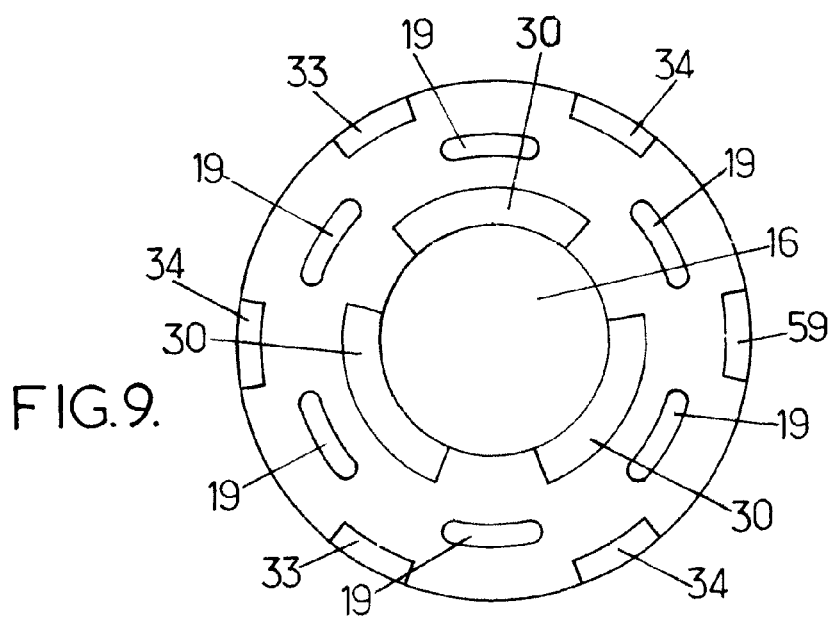
FIG. 9 is a sectional view along line IX-IX of FIG. 8a, FIG. 10 is a partial perspective view of a probe according to a fifth embodiment.

According to a fourth embodiment, as shown on FIGS. 8a, 8b and 9, the probe comprises only two components. Indeed, the combined applicator and ultra-sound device 39 of the third embodiment (FIG. 7a) is modified to incorporate the fluid micro circuitry which, in the third embodiment, is provided through the independent cooling mandrel 41. Thus, in the fourth embodiment, as shown on FIG. 8a, in addition to the features of the combined device of the third embodiment, an in-flow channel extends from the in-flow aperture 17 provided in the head 14, whereas the internal cavity 16 itself serves as the out-flow channel. The in-flow channel 19 is thus in fluid communication with the cavity 16 at the insertion tip 9 of the device.

In this fourth embodiment, the probe still comprises the rigid mandrel 12 of the two previous embodiments.

Figure 10:
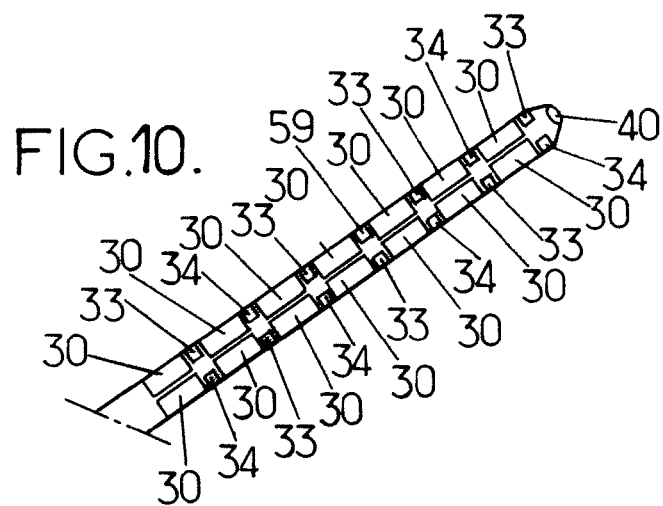

A fifth embodiment is partially shown on FIG. 10. This fifth embodiment differs from the third or fourth embodiment in that it has no side openings.

Figure 11A:
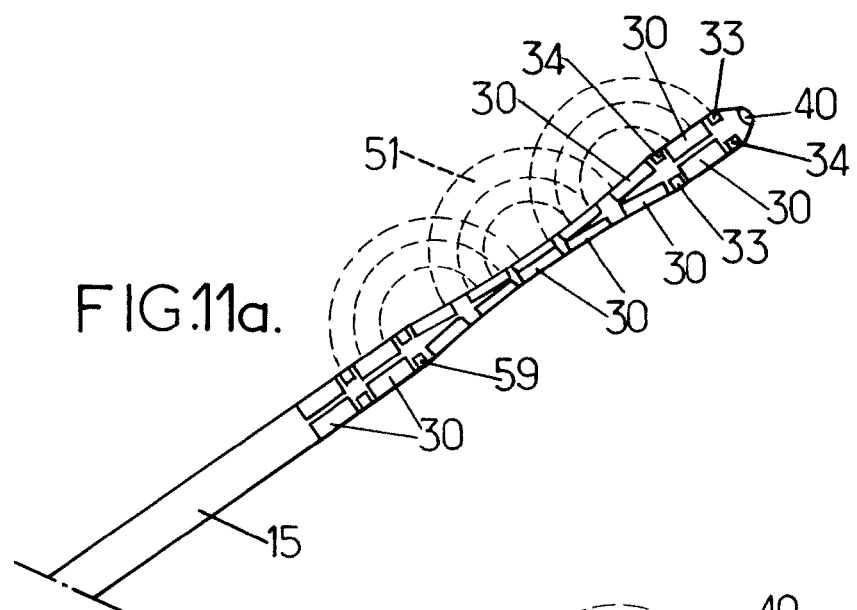
FIGS. 11a and 11b are partial perspective views of probes according to a sixth and a seventh, respectively, embodiment.
Figure 11B:
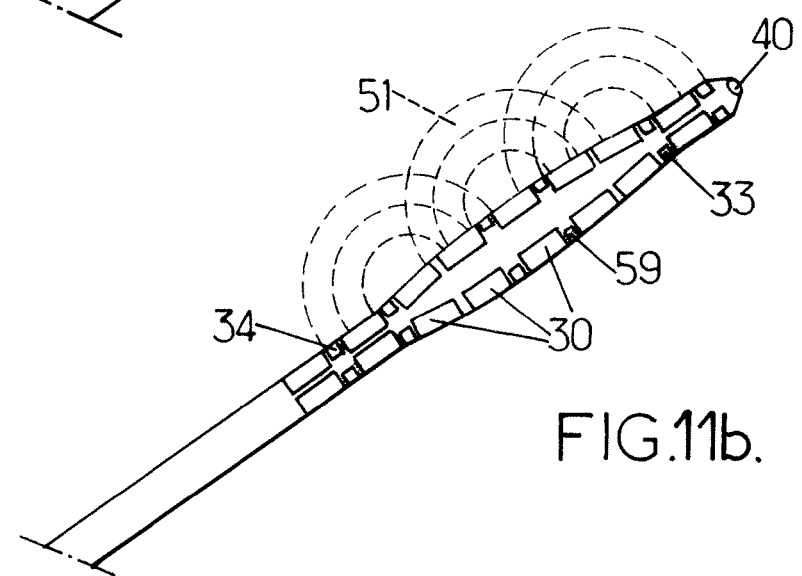

FIG. 11a partially shows a sixth embodiment of a device 39. When compared to the device of the fifth embodiment, this sixth embodiment differs by a concave arrangement of the transducers, for example in a central portion of the device 39. For example, no sensors are found in this central portion. Thus, instead of being purely cylindrical, the body 15 has, in this embodiment, a thinned central portion. According to another embodiment, as shown on FIG. 11b, the central portion could be convex.

Such convex or concave shapes could be used for any of the ultra-sound carrying components of the above embodiments.

It is contemplated that other geometries could be used provided the ultra-sound device is still able to provide therapeutic ultra-sound energy with the required power.

The ultra-sound waves 51 are schematically illustrated on these figures.

FIG. 12 now describes a schematic representation of an embodiment of the computerized system 5. This system could be embodied on one or on a plurality of programmable machines and comprise both hardware and software components. The operating system and interfaces of the computerized system can be of any conventional type, and will not be described in more details here. The system 5 comprises network corrections, data archiving and storage software and hardware, image manipulation software including metric and editing functions, . . . .

The computerized system 5 can comprise an echographic and elastographic imaging software 43 of conventional type suitable for obtaining a 2D or a 3D image based on ultra-sound detection data provided from the probe 6, and resulting from the detection by the probe 6 of ultra-sound emitted by the probe 6 and reflected by the organ.

The computerized system can further comprise an EEG-reading software 44 adapted to read data provided from the probe 6, and detected by the electro-physiological sensors 33 of the probe.

The computerized system can further comprise a thermal software 47 receiving data from the temperature sensors 34 of the probe 6 and adapted to determine temperature data of the tissue based on these received signals.

The computerized system can further comprise a confocal microscope image software 48 adapted to receive data from the confocal microscope head 23 of the probe 6, and to form an image from this data.

The computerized system 5 can further comprise an MRI image software 45 receiving data from the MRI system 2 and adapted to reconstruct an MRI anatomy image of the patient from this data in conventional way.

The computerized system can further comprise a thermal image software 46 connected to the MRI system 2 and adapted to treat data provided from the MRI system 2 to provide the user with a thermal image and with thermal ablation image of the patient.

The computerized system 5 can further comprise a planning software 49 adapted to gather information and/or data about the patient and/or the studied organ and/or region from the echographic imaging software 43, the EEG software 44, the MRI image software 45, the confocal microscope image software 48, as well as if necessary, any other patient data, or organ data, obtained by any other suitable way. The planning software 49 enables the clinician to evaluate the relevant information, and to determine the best suit of action for the patient.

The computerized system can further include a simulation software 60 that can elaborate the optimal parameter settings for the treatment, based on the various information available.

For example, the simulation software 60 will use a model of the probe (including its position and orientation in the patient's reference frame, for example obtained from the MRI), a model of the tumor (acoustic impedance and other relevant parameters), and the geometry of the planned ablation, to estimate the appropriate settings to use for each of the transducers.

The computerized system 5 can further comprise a command software 50 adapted to gather information from the planning software 49, the MRI thermal image software 46, the thermal software 47. The command software 50 comprises a setting device 55 enabling to set the probe 6 in therapeutic or fragmentation mode (see below), by setting the parameters of the ultra-sound transducers to emit the necessary ultra-sound energy, as determined from the simulation and the planning software 49, toward the appropriate region (appropriate focal area) of the patient. The ultra-sound can be set to operate in thermal- and/or cavity-dominant modes, and the focal area can be dynamically modified, for example under MRI image guidance, or ultra-sound imaging.

The command software 50 can also be used to operate the other mechanical parts of the system such as the pump 22, through a pulsed-pump command 53, the pump 36 through a continuous pump command 54, and the ultra-sound device in imaging mode, through the setting device 55. The command software 50 is connected to power amplifiers 56 which deliver the necessary power to the transducers 30. The switch between the different operation modes of the transducers could be commanded by a foot switch operated by the clinician.

In the therapeutic mode, the system can operate in a step-by-step user-commanded style, or in a computer-controlled automatic style.

FIG. 13 now describes a possible application of the above described medical system.

At step 101, the applicator 11 comprising the inner rigid mandrel 12 is percutaneously inserted into the tissue of the patient's organ, either by hand or under image monitoring (external echography or MRI). Alternatively, a stereotaxis frame or a robot arm could be used, for example for cerebrally inserting the probe.

At step 102, the position of the probe relative to the organ is monitored. For example, an image of the patient is obtained from the MRI system, or from an external CT-scan or echographic system. In alternative or in addition, the image could be obtained by the probe 6 itself, operating in an "imaging" mode. To do so the mandrel has to be removed and the ultra-sound device 13 inserted. In this mode, the ultrasound transducers 30 are commanded, by the command software 50, to operate in an imaging mode, in which they emit ultra-sounds, for example within the operation volume 37, and to detect the reflected ultra-sounds, the obtained detection data being thus sent to the echographic imaging software 43 of the computerized system.

At step 103, the inner rigid mandrel 12 is removed while simultaneously bringing liquid through the channel 27 by the pump 36 to avoid air introduction. The continuous pump 36 is then directly connected to the internal cavity 16, so as to perform a biopsy by aspirating through the opening(s) 40, a part of the organ. Alternatively, a syringe head or a biopsy needle could be used. This part can be further analyzed to confirm the characteristics of the tissue. In addition or in alternative, tissue characterization could be performed by disconnecting the pump 36 and inserting the microscope optical fiber through the cavity 16 (or 27), so as to use the endo-confocal microscope, the data of which is provided to the confocal microscope image software 48 of the computerized system.

At step 104, data from the electro-physiologic sensors 33 is obtained and is forwarded to the electro encephalogram reading software 44 of the computerized system 5.

Using the data obtained at steps 102, 103, and/or 104, at step 105, the target volume and the probe position in reference to the targeted volume are defined, for example by the clinician using the planning software 49. The target volume can further be defined manually or automatically, using external images, such as MRI images or the like.

Based on the location and size of the target volume, at step 105', the therapeutic ultra-sound energy, phases, durations for the various ultrasound transducers are simulated and calculated. At step 106, the ultra-sound emission parameters are set, for example using the command software 50. The size and the location of the focal area, the ultra-sound power and frequency are set in the command software 50. Low frequency ultra-sound waves can be used for applying therapeutic ultra-sound energy to regions remote from the probe 6, whereas higher frequencies can be used for close regions. The probe 6 is thus set to operate in a thermal "therapeutic" treatment mode, either by non destructive (metabolism stimulation, . . . ) or destructive (coagulation, vaporization) mode.

Figure 14:
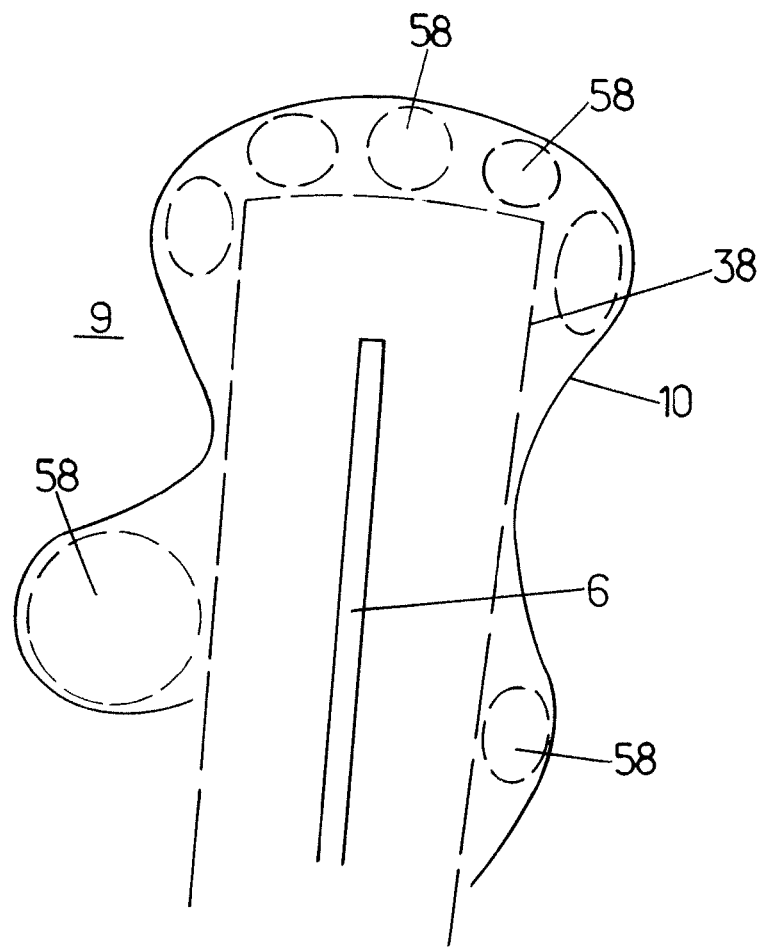
FIG. 14 is a enlarged view of FIG. 2.

At step 107, the ultra-sounds are delivered to the region 10 of the organ 8. As shown on FIG. 14, the probe 6 could be operated in de-focused mode inside the envelope 38. It can also be operated in a focused mode active on specific focal areas 58. Simultaneously, cooling physiological fluid is pumped into the micro-circuitry of the probe by the pump 22, under command of the command software 50, so as to efficiently cool the probe. Real-time thermal MRI images are provided to the thermal image software 46 of the computerized system for monitoring the temperature rise in the probe and/or in the organ and/or security points for the treatment. Necrosis prediction could be performed by the computerized system 5 by summing in time the obtained thermal data, to obtain thermal deposited doses within the specific volume. The reflected ultra-sounds are detected by the transducers 30, and real-time images are formed at the computerized system 5, which enables a real-time ultra-sound monitoring.

At step 108, the efficiency of the therapy ultra-sound application is monitored, for example from the detected MRI image, or by ultra-sound imaging (echography, elastography). If the therapeutic treatment is not judged sufficient by the clinician, the process continues back from step 105. However, if the clinician finds out that a sufficient thermal treatment was performed, the process moves to step 109.

At step 109, the treated region 10 is mechanically fragmented by ultra-sounds. The probe 6 is set to operate in a "fragmentation" mode by emission of pulsed ultra-sound to the treated region of the organ. The "fragmentation" mode also is a therapeutic mode. This results in a fragmentation (shearing) of the region, by breaking the inter-cellular adhesions using the jet-steam/cavitation technique. Of course, the ultra-sound parameters, in this mode, can be set from the command software 50. In this mode, the probe is continuously cooled by the pump 22. In another method, the fragmentation of the tissue can be performed by low frequency vibration (around 10 kHz [1-50 kHz]) emitted by the electro-mechanical mandrel back portion 26 through the mandrel body (if reintroduced) to transmit low frequency vibration within the treated tissue, or alternatively by yet another specific mechanical-stress inducing mandrel.

At step 110, the efficiency of the fragmentation step 109 is monitored. If this step is not judged sufficiently efficient by the clinician, the process moves back to step 109 whereas, if it is judged to be sufficiently efficient, the process moves to step 111 where the fragmented tissue is aspirated outside the body.

At step 111, the optical fiber of the endo-confocal microscope is removed, the pump 36 connected to the cavity performs a soft aspiration, at controlled negative pressure, commanded by the command software 50 of the computerized system, so as to allow the decrease in volume of the treated region.

At step 112, it is monitored whether the treatment can be judged satisfactory by the clinician. If this is not the case, the process moves back to step 111. If it is decided to end the procedure, the probe 6 is removed from the organ and the process is ended.

The above description is just an exemplary description of one possible embodiment of the above described probe and system and it is within the reach of the person skilled in the art to repeat, bypass, or change the order of the above steps, or to add additional steps, dependent of the pathology to be treated. Thus, the probe could allow the treatment of the tissue lesions by the following modes and physical agents: thermal blood coagulation, thermal reversible ischemia, non-thermal mechanical jet steam and cavitation means, sonoporation or combinations thereof.

Furthermore, the interstitial probe could be used in a non-interstitial way, by being placed in close proximity, but outside an organ to be treated. The probe could be disposable, or be sterilized between subsequent uses.

Furthermore, in another embodiment, the probe could be permanently installed in the organ of the patient, and be remote-controlled by a suitable computer, for example implanted inside the patient, at periodical examinations.

Although the above embodiments show a probe having numerous features, it should be noted that not all of these features necessarily need to be part of the inventive probe. For example, the information collection device could be comprised of only one or more of the ultra-sound transducers 30 in imaging mode, the electro physiological sensors 33, the temperature sensors 34, and the endo-confocal microscope head 40.

The invention claimed is:

1. A percutaneous probe of MRI-compatible materials, the percutaneous probe comprising:
    a body made of MRI-compatible materials and having an insertion end shaped to be percutaneously inserted into tissue of a patient's body organ having a region to be analyzed, treated and monitored during a single medical procedure, the body of the percutaneous probe including a cavity, the cavity being configured to insert fluid into the patient through an opening in the insertion end of the body, to collect a part of said tissue from the patient's body through the opening, and to decrease in volume said region of the organ after treatment by allowing substances to be aspirated through the opening into the cavity,
    a rigid mandrel shaped to be inserted into the cavity,
    at least one information collection sensing device, adapted to collect information about the region of the organ, and
    a plurality of treatment application transducers disposed all around a circumference and a length of a part of the body of the probe which is to be inserted in the region to be treated, the plurality of treatment application transducers being operable as a phased-array, adapted to emit both focused and not-focused therapeutic ultra-sound waves to the region of the organ.

2. The percutaneous probe according to claim 1, wherein the information collection sensing device comprises at least one ultra-sound transducer adapted to perform ultra-sound imaging of the body organ, and
    wherein each transducer is adapted to be operated in an imaging mode, wherein it operates as the information collection sensing device, and in a therapeutic mode, wherein it operates as the treatment application transducer.

3. The percutaneous probe according to claim 1, comprising an aspiration device adapted to collect the part of said tissue from the patient's body through the cavity of the probe body.

4. The percutaneous probe according to claim 1, wherein the information collection sensing device comprises at least one of the following:
    at least one electro-encephalography electrode adapted to collect brain physiological signals,
    at least one biosensor adapted to collect tissue physiological signals,
    at least one thermal electrode adapted to measure the temperature of the region,
    a biopsy needle adapted to collect tissue.

5. The percutaneous probe according to claim 1, comprising fluid evacuation circuitry, adapted to evacuate fluid from the organ through the probe body.

6. The percutaneous probe according to claim 1 comprising fluid circuitry adapted to allow a cooling fluid to flow in the probe body.

7. The percutaneous probe according to claim 1 wherein treatment application transducers are adapted to generate a temperature rise of at least 30° C., within less than 1 s, in a treatment region of spherical shape of at least 2 mm in diameter neighbouring the treatment application device.

8. The percutaneous probe according to claim 1 wherein the treatment application transducers are adapted to generate a temperature rise of at least 30° C., within less than 10 nm, within a envelope of 30 mm of cross-sectional diameter around the probe.

9. The percutaneous probe of claim 1, further comprising an optical head of an endo-confocal microscope.

10. The percutaneous probe according to claim 1, wherein the transducers are arranged in a convex manner on the body of the percutaneous probe.

11. A medical system comprising:
    a percutaneous probe of MRI-compatible materials, the percutaneous probe including:
    a body made of MRI-compatible materials and having an insertion end shaped to be percutaneously inserted into tissue of a patient's body organ having a region to be analyzed, treated and monitored during a single medical procedure, the body of the percutaneous probe comprising a cavity, the cavity being configured to insert fluid into the patient through an opening in the insertion end of the body, to collect a part of said tissue from the patient's body through the opening, and to decrease in volume said region of the organ after treatment by allowing substances to be aspirated through the opening into the cavity,
    a rigid mandrel shaped to be inserted into the cavity,
    at least one information collection sensing device, adapted to collect information about the region of the organ, and
    a plurality of treatment application transducers disposed all around a circumference and a length of a part of the body of the probe which is to be inserted in the region to be treated, the plurality of treatment application transducers being operable as a phased-array, adapted to emit both focused and not-focused therapeutic ultra-sound waves to the region of the organ; and
    a computerized system comprising a parametrizable command device and associated equipment adapted to command a generation of the therapeutic ultra-sound wave.

12. The medical system according to claim 11, wherein the computerized system comprises an imaging device adapted to generate an image from sensed ultra-sound.

13. The medical system according to claim 11 wherein the percutaneous probe comprises fluid circuitry adapted to allow a cooling fluid to flow in the probe body, and wherein the computerized system comprises a pulsed pump command adapted to generate a flow of the cooling fluid in the probe body.

14. The medical system according to claim 11, wherein the percutaneous probe comprises an aspiration device adapted to collect the part of said tissue from the patient's body through the cavity of the probe's body, wherein the computerized system comprises a continuous pump command adapted to aspirate through the probe body.

15. The medical system according to claim 11, wherein the computerized system comprises at least one power amplifier adapted to generate and transfer to the treatment application transducers a power sufficient for emission of the therapeutic ultra-sound waves to the region of the body organ.

16. The medical system according to claim 11, wherein the computerized system comprises a setting device adapted to set parameters of the therapeutic ultra-sound waves.

17. The medical system according to claim 11, wherein the computerized system comprises an MRI interface adapted to be connected to an MRI system and to receive MRI data of the patient's body therefrom, and software adapted to generate and manipulate MRI images.

18. The medical system according to claim 11 wherein the computerized system further comprises software adapted to generate and manipulate at least ultra-sound and confocal microscopy images.

19. The medical system according to claim 11, wherein the computerized system includes a simulation software adapted to determine parameters of the therapeutic ultra-sound waves.

20. The medical system according to claim 19, wherein the simulation software is adapted to model the probe and the geometry of region of the organ to be analyzed, treated and monitored to estimate said parameters.

21. A medical system according to claim 11, wherein the percutaneous probe comprises fluid circuitry adapted to allow a cooling fluid to flow in the probe body, wherein the computerized system comprises a continuous pump command adapted to aspirate through the probe body.

22. The medical system according to claim 11, wherein the transducers are arranged in a convex manner on the body of the percutaneous probe.

23. A method of analyzing, treating and monitoring a region of a body organ having a region to be analyzed, treated and monitored during a single medical procedure, the method comprising:
inserting an insertion end of a percutaneous probe into tissue of the body organ by using a rigid mandrel shaped inserted into a cavity of the body of the percutaneous probe, wherein the percutaneous probe is made from MRI compliant materials and comprises a body,
removing the rigid mandrel while simultaneously bringing fluid through the cavity after inserting the insertion end of the percutaneous probe into tissue of the body organ
collecting information about the region of the organ with an information collection sensing device of the probe by performing a biopsy through the cavity,
setting parameters of at least one of a focused and not-focused therapeutic ultra-sound waves to be emitted to the region of the organ with a plurality of treatment application transducers of the probe disposed all around a circumference and a length of a part of the body of the probe which is to be inserted in the region to be treated, the plurality of treatment application transducers being configured as a phase-array through a parametrizable command device and associated equipment of a computerized system,
after treatment, decreasing in volume said region of the organ by aspiring substances from the patient's body through the cavity.

24. The method according to claim 23 further comprising performing an analysis of the collected information and setting parameters of the therapeutic ultra-sound waves based on said analysis.

25. The method according to claim 23 further comprising emitting said therapeutic ultra-sound waves.

26. The method according to claim 25 further comprising monitoring an efficiency of the therapy ultra-sound waves.

27. The method according to claim 23 further comprising performing the biopsy by aspirating through the cavity a part of the body organ.

28. The method according to claim 23, further comprising collecting information about the region of the organ with an information collection sensing device of the probe, and with an optical head of an endo-confocal microscope.

29. The method according to claim 23, wherein the transducers are arranged in a convex manner on the body of the percutaneous probe.

* * * * *